United States Patent [19]

Li et al.

[11] Patent Number: 5,449,615

[45] Date of Patent: Sep. 12, 1995

[54] KDN-CLEAVING SIALIDASE ISOLATED FROM HEPATOPANCREAS OF MOLLUSKS

[76] Inventors: Yuh-Teh Li; Su-Chen Li, both of 1717 Old Metairie Rd., Metairie, La. 70001

[21] Appl. No.: 311,957

[22] Filed: Sep. 26, 1994

[51] Int. Cl.$^6$ .......................... C12N 9/24; C12N 9/36
[52] U.S. Cl. ...................................... 435/200; 435/206
[58] Field of Search ................................ 435/206, 200

[56] References Cited

PUBLICATIONS

Ghosh et al., Anal. Biochem, 196, 252–261, 1991.
Lee et al., Comp. Biochem. Physiol., vol. 99B, No. 4, 845–850–1991.
Chuang et al., Comp. Biochem. Physiol., vol. 96B, No. 4, 747–51, 1990.
Chuang et al., Comp. Biochem. Physiol., vol. 97C, No. 2, pp. 353–356, 1990.
Li et al., Glycobiology, vol. 3, No. 5, Oct. 1993, p. 525.
Li et al., The 8th Rinshoken Int'l Conference–"Frontier in Glycobiology and Glycotechnology", Abstract, Sep. 27–29, 1993, p. 121.
Li et al., Archives of Biochemistry and Biophysics, v. 310, N. 1, 243–46, 1994.

Primary Examiner—David M. Naff
Assistant Examiner—Michael Meller
Attorney, Agent, or Firm—Joseph T. Regard, Ltd.

[57] ABSTRACT

A sialidase capable of cleaving a glycoconjugate to yield 3-deoxy-D-glycero-D-galacto-2-nonulosonic acid (KDN) is isolated from hepatopancreas of mollusks. Preferably, the sialidase is isolated by processing crude oyster hepatopancreas to form a crude extract of the sialidase enzyme. The crude enzyme is further concentrated and refined utilizing sequential column chromatography fractogel EMD DEAE-650 (M), sephacryl S-200, and fractogel EMD SP 650 (M) chromatography, respectively. Using this procedure, the sialidase is purified over 155 fold with a 17% recovery. Ferric ion exerts a three fold stimulation in the activity of the sialidase, at a concentration of 3 mM. The sialidase cleaves 4-methylumbelliferyl-KDN, KDNα2→3Galβ1→4GlcCer, KDNα2→6Galβ1→4GlcCer, or KDNα2→6GalNAc-ol to yield KDN.

2 Claims, 7 Drawing Sheets

Figure 1d

TABLE I

*Purification of KDN-cleaving sialidase from 100g of oyster acetone powder*

| Purification step | Total activity | Total protein | Specific activity | Recovery | Purification |
|---|---|---|---|---|---|
| | (units x $10^{-3}$) | (mg) | (units/mg) | (%) | (-fold) |
| Crude Extract | 69.7 | 11,400 | 6.1 | 100 | 1.0 |
| Fractogel EMD DEAE 650 (M) | 65.2 | 2,442 | 26.7 | 94 | 4.4 |
| Sephacryl S-200 | 61.0 | 637.0 | 96 | 88 | 15.7 |
| Fractogel EMD SP 650 (M) | 26.8 | 80.0 | 334 | 38 | 54.8 |
| Octyl Sepharose CL-6B | 13.4 | 18.4 | 730 | 19 | 120.0 |

Sephacryl S-200

KDN-CLEAVING SIALIDASE ISOLATED FROM HEPATOPANCREAS OF MOLLUSKS

U.S. GOVERNMENT FUNDING STATEMENT

This invention was made with government support under a grant awarded by the National Institute of Health.

TECHNICAL FIELD OF THE INVENTION

This invention relates to the isolation of a KDN-cleaving sialidase (KDN-sialidase) from the hepatopancreas of oysters and other mollusks, and the novel enzyme of same.

BACKGROUND OF THE INVENTION

KDN (2-keto-3-deoxy-D-glycero-D-galacto-nononic acid, which is synonymous with 3-deoxy-D-glycero-D-galacto-2-nonulosonic acid and "deaminated neuraminic acid") is a novel sialic acid first isolated from the polysialoglycoproteins of rainbow trout (*Salmo gairdneri*) eggs. (Nadano, D. et al., (1986) J. Biol. Chem. 261: 11550–11557; Iwasaki, M. et al, (1987) Biochemistry 26:1452–1457; Inoue, S. et al., (1988) Biochem. Biophys. Res. Commun. 153:172–176).

Subsequently, KDN-containing glycoconjugates have been discovered throughout nature including in the sperm of rainbow trout (Song, S. et al., (1991) J. Biol. Chem. 266:21929–21935), the jelly coat of the eggs of the newt *Pleurodeles waltlii* (Strecker, G. et al., (1992) FEBS Lett. 298:39–48) and the capsule of the bacterium *Klebsiella ozaenae* (Knirel, Y. A. et al., (1989) Carbohydr. Res. 188:145–155.

KDN-containing glycoconjugates are refractory to regular sialidases. FIG. 1c shows the specificities of KDN-cleaving sialidase (KDN-sialidase) and regular sialidase.

Li, et al., made a poster presentation of the presence of a KDN-cleaving sialidase in the liver of the loach, *Misgurnus fossilis* at the Rinshoken International Conference, Tokyo, Japan, Sep. 27-29, 1993. Li, et al., also presented the same material at the 22nd annual meeting of the Society for Complex Carbohydrates in Puerto Rico, Nov. 17–20, 1993, *Glycobiology*, volume 3, p. 525, 1993. Subsequently, Li, et al., reported the partial purification of KDN-cleaving sialidase from loach liver (Li, Y.-T. et al.,). Arch. Biochem. Biophys. (1994) 310:243–246, the contents of which are incorporated herein by reference.

A KDN-cleaving enzyme called KDNase has also been recently induced in a microorganism, *Sphmgobacterium multivorum* (Kitajima, K., et al., J. Biol. Chem. (1994) 269:21415–21419). A detailed method for the isolation of KDN-cleaving sialidase from mollusks has never been described. The KDN-cleaving sialidase is an indispensable tool for the detection and characterization of KDN-containing glycoconjugates and for studying their biological function. No convenient source and method are currently available for facile preparation of a KDN-cleaving sialidase.

We discovered that the hepatopancreases of mollusks are rich in KDN-containing sialidase. The present invention describes a method for facile isolation of KDN-cleaving sialidase from a mollusk, using as an example, a marine bivalve lamellibranch mollusk of the family Ostreidae, an oyster.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 1D illustrates, in table form, the purification of the KDN-cleaving sialidase of the present invention from an exemplary g of oyster acetone powder.

DETAILED DISCUSSION OF THE INVENTION

Fluorometric assay of the KDN-cleaving activity using 4-methylumbelliferyl-KDN as substrate is used to follow the purification of KDN-cleaving sialidase. (See Potier, M., et al., Anal. Biochem. (1979) 94:287–296). The assay mixture contains the following components: 4-methylumbelliferyl-KDN, 20 nmol; sodium acetate buffer, pH 5.5, 5 $\mu$mol; and an appropriate amount of enzyme. 100 $\mu$l of assay mixture is used for each assay.

After the mixture is incubated at 37° C. for a predetermined period of time, the reaction is terminated by the addition of 1.5 ml of 0.2 M sodium acetate buffer, pH 9.8 to the assay mixture. The concentration of free 4-methylumbelliferone is determined by a spectrofluorometer. One unit of activity (4-methylumbelliferyl-KDN-cleaving activity) is defined as the amount of enzymic activity necessary to liberate 1 nmol of 4-methylumbelliferone per minute at 37° C.

The free KDN released from sialoglycoconjugates is also analyzed by thin-layer chromatography (TLC). Briefly, the reaction mixture contains 30 nmoles of substrate in 30 $\mu$l of 50 mM sodium acetate buffer, pH 4.0 and an appropriate amount of enzyme. After incubating at 37° C. for a preset time, the reaction is stopped by the addition of 20 $\mu$l ethanol followed by centrifugation. A 10 $\mu$l aliquot from each incubation is applied to a pre-coated silica gel-60 TLC plate.

The plate is developed by n-butanol:acetic acid:water (2/1/1/, v/v/v) and sprayed with diphenylamine reagent. We have shown that diphenylamine reagent can conveniently reveal and distinguish KDN and NeuAc on TLC plates:NeuAc gives a distinctive pink color and KDN, a purple color (Li, Y-T. et al., Arch. Biochem. Biophys. (1994) 310:243–246).

Figure 1A:
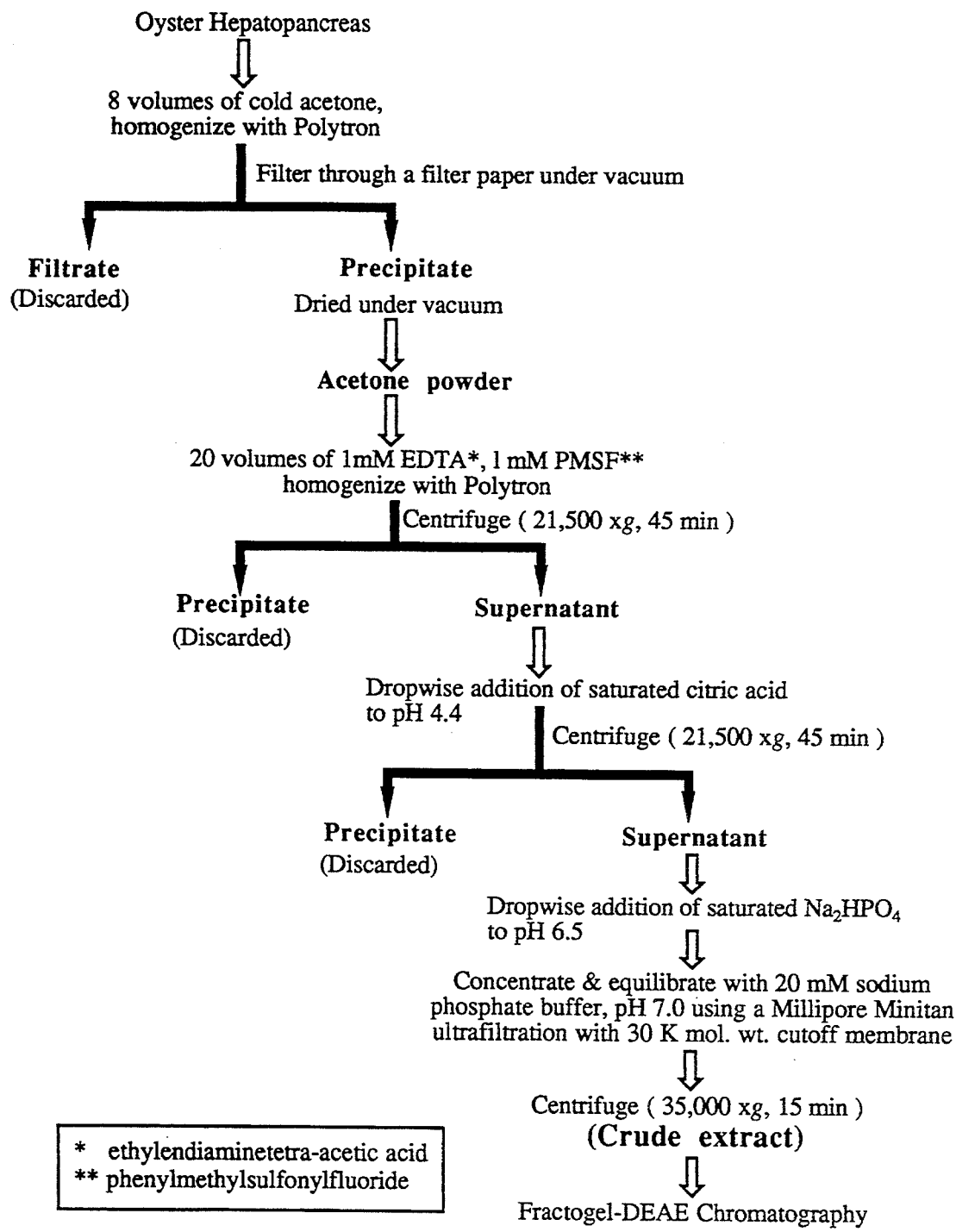
FIG. 1a illustrates the method of preparing KDN-Cleaving Sialidase from the hepatopancreas of an exemplary mollusk, an oyster.
Figure 1B:
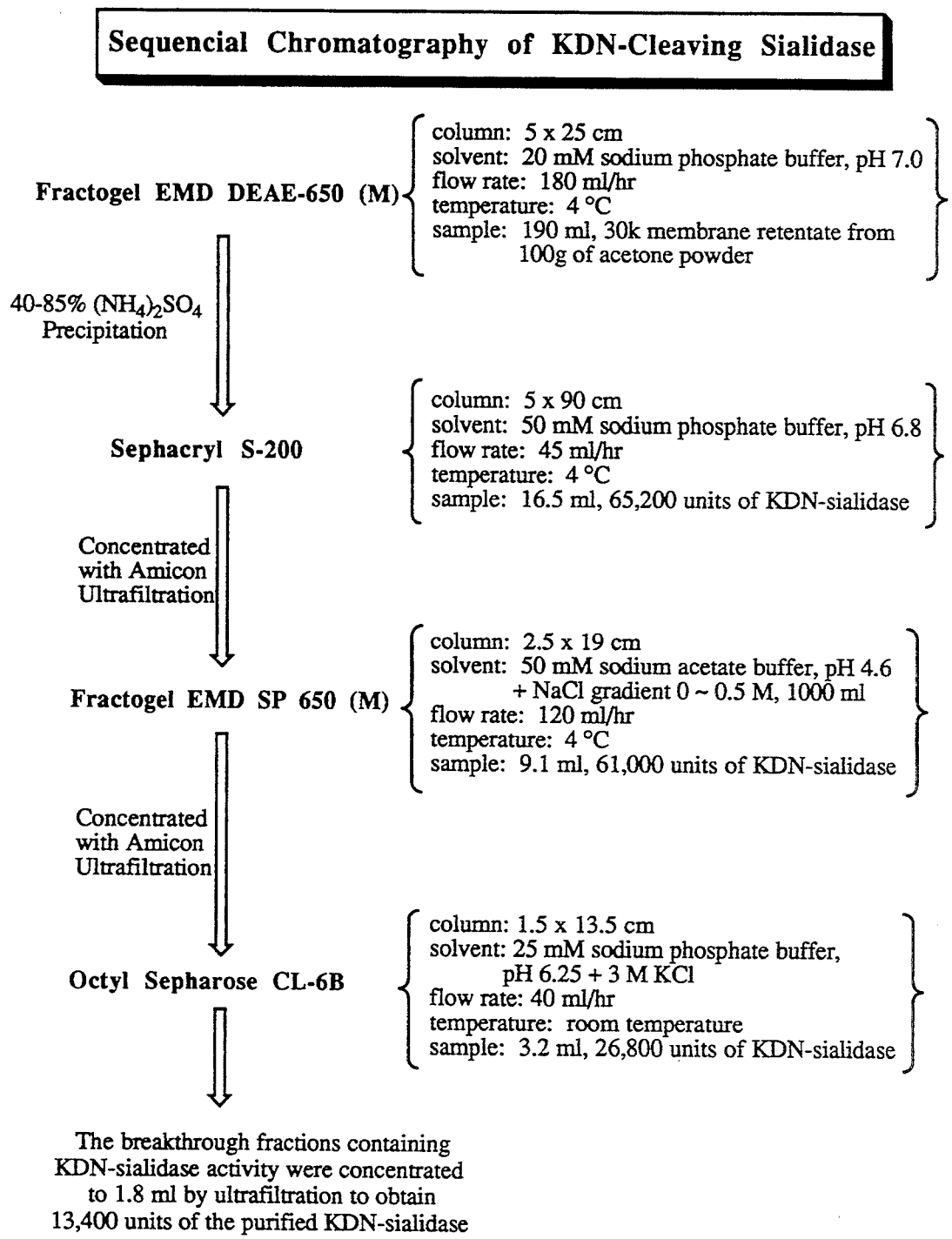
FIG. 1b illustrates the sequential chromatography of the KDN-cleaving sialidase of the present invention.
Figure 1C:
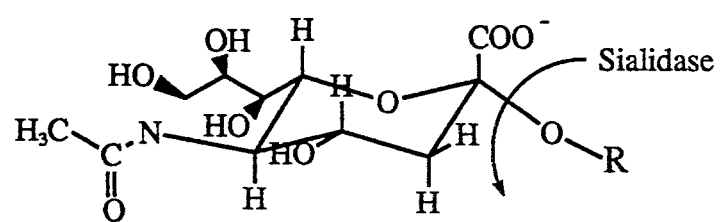
FIG. 1C illustrates the enzymatic reaction of regular sialidase (sialidase) and KDN-cleaving sialidase (KDN-sialidase).
Figure 1C:
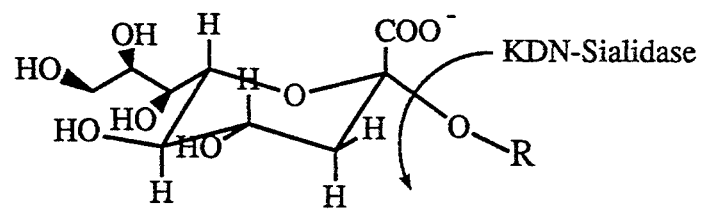

The procedures for extraction and purification of KDN-cleaving sialidase from oysters are summarized in Schemes 1 and 2 (FIGS. 1a and 1b).

Unless otherwise indicated, the isolation of KDN-cleaving sialidase is carried out at a temperature between 0° and 5° C. Centrifugation is routinely carried out 10,000 to 20,000 xg for 30 minutes using a refrigerated centrifuge. Unless otherwise indicated, ultrafiltration is carried out with an Amicon ® stirred cell using PM 10 membrane.

For preparing KDN-cleaving sialidase from oysters, hepatopancreases are removed from oysters using a pair of scissors. Oyster hepatopancreases are homogenized with 8 volumes of cold acetone using a polytron homogenizer, filtered with a Buchner funnel and dried under vacuum to obtain, for example, 73 g of oyster acetone powder. The oyster hepatopancreas acetone powder is then extracted with water containing 1 mM ethylenediamine-tetraacetic acid and 1 mM phenylmethylsulfonylfluoride added as protease inhibitors, using a polytron homogenizer, followed by centrifugation to obtain a crude extract.

This crude extract is brought to pH 4.4 by the dropwise addition of saturated citric acid solution, while stirring. The precipitate formed is removed by centrifugation and the pH of the clear supernatant is quickly adjusted to 6.5 by the dropwise addition of a saturated $Na_2HPO_4$ solution and concentrated by ultrafiltration with, for example, a Minitan TM acrylic tangential flow ultrafiltration system (Millipore) using 30,000 NMWL cut-off PTMK polysulfone membrane plates. The precipitate formed during concentration is removed by centrifugation to obtain a crude enzyme preparation.

Figure 2:
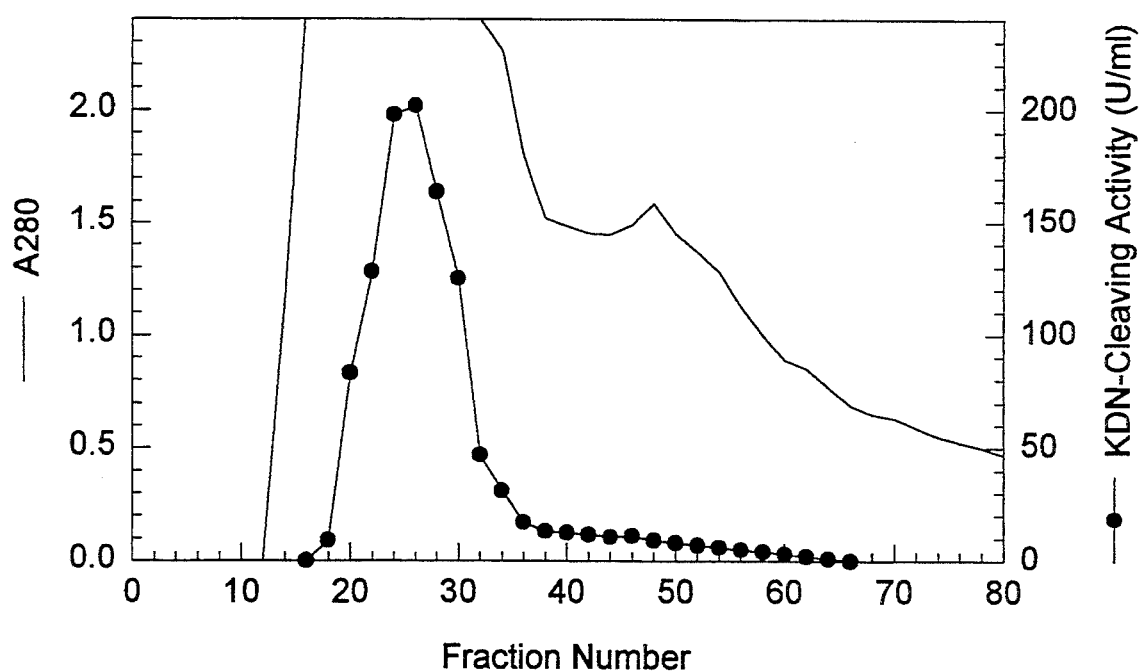
FIG. 2 shows the elution pattern for the purification of KDN-cleaving sialidase using Fractogel EMD DEAE-650 (M) chromatography.
Figure 3:
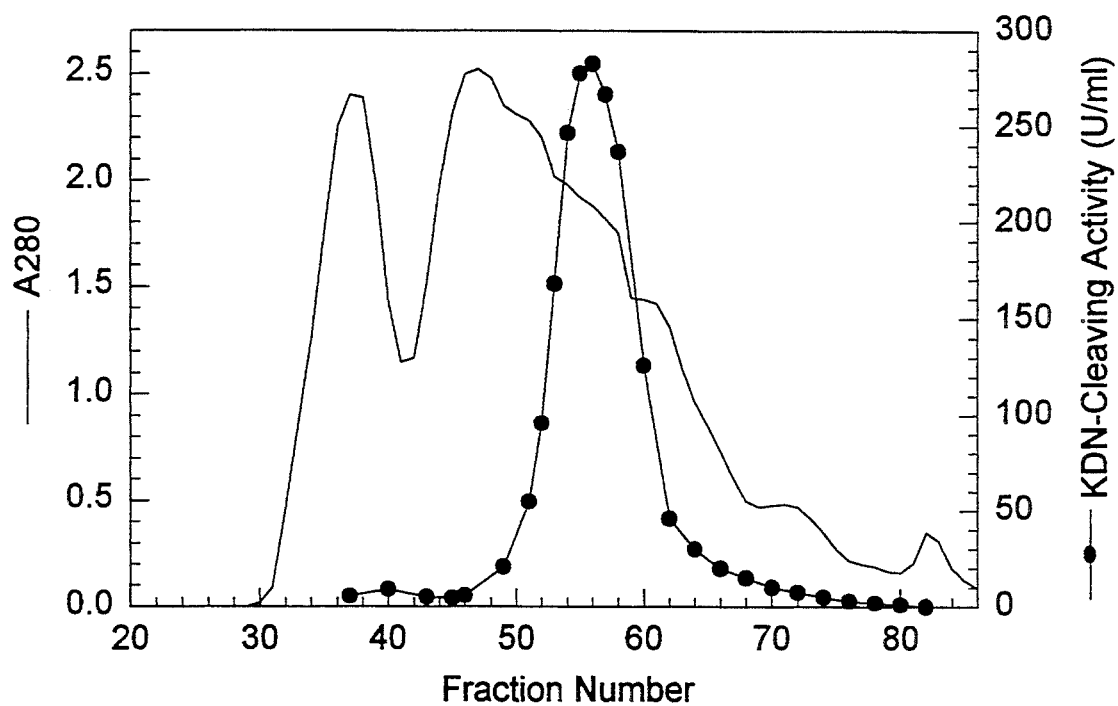
FIG. 3 shows the elution pattern for the purification of KDN-cleaving sialidase using Sephacryl S-200 chromatography.
Figure 4:
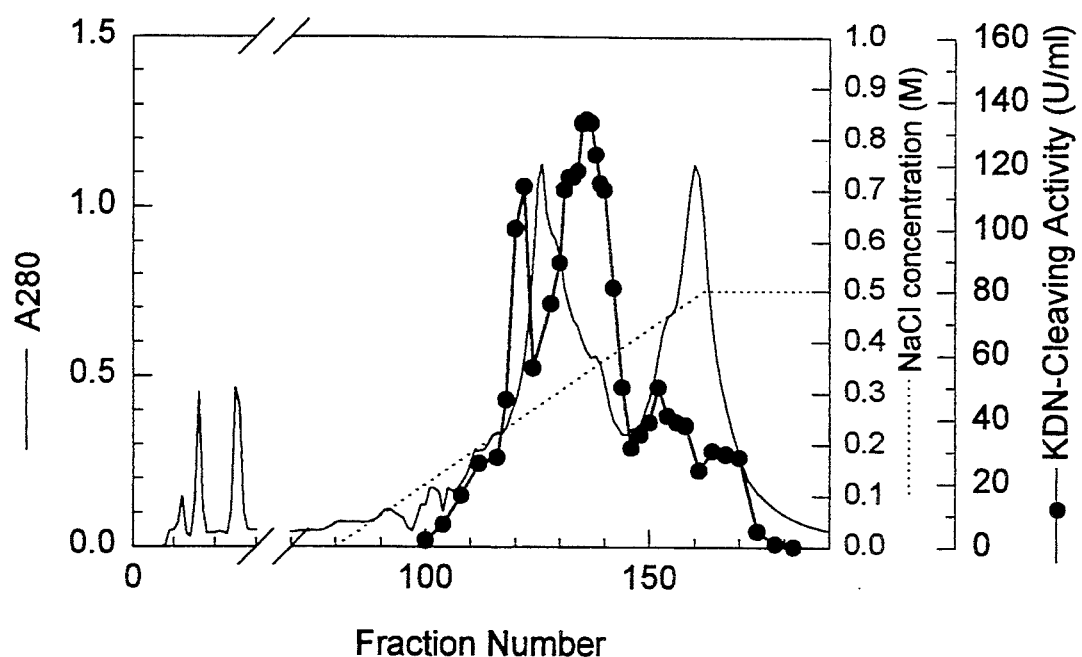
FIG. 4 shows the elution pattern for the purification of KDN-cleaving sialidase using Fractogel SP 650 (M) chromatography.

This crude enzyme preparation is then purified by sequential column chromatography as shown in Scheme 2 (FIG. 1b). FIGS. 2–4 depict the sequential chromatographic purification of KDN-cleaving sialidase using Fractogel EMD DEAE-650 (M) chromatography (FIG. 2), Sephacryl S-200 chromatography (FIG. 3) and Fractogel EMD SP 650 (M) chromatography (FIG. 4).

Using the procedures described above, KDN-cleaving sialidase is purified over 155 fold with a 17% recovery (FIG. 1d). The molecular weight of KDN-cleaving sialidase is found to be 21,000 using gel filtration. The optimal pH of the enzyme is between 3.8 and 4.5 and the enzyme is stable between pH 3.8 and 7.5. The isoelectric point for the KDN-cleaving sialidase is determined to be 7.6 by chromatofocusing. This is the first known sialidase capable of efficiently cleaving glycosidically linked KDN.

Unlike regular sialidase, KDN-cleaving sialidase is not inhibited by 2,3 anhydro N-acetylneuraminic acid. KDN-cleaving sialidase is stimulated by the presence of ferric ion. Ferric ion at the concentration of 3 mM exerts a three fold stimulation on the activity of KDN-cleaving sialidase. Ferric ion, on the other, hand does not affect the activity of regular sialidase.

The novel sialidase efficiently hydrolyzes KDN from the 4-methylumbelliferyl$\alpha$-ketoside of KDN, KDN$\alpha$2→3Gal$\beta$1→4GlcCer, KDN$\alpha$2→6Gal$\beta$1→4GlcCer, and KDN$\alpha$2→6N-acetylgalactosaminitol. These KDN-containing glycoconjugates are refractory to regular sialidases.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. An isolated sialidase from hepatopancreas of mollusks capable of cleaving glycoconjugates to yield 3-deoxy-D-glycero-D-galacto-2-nonulosonic acid (KDN), wherein said sialidase has a molecular weight of about 21000 daltons using gel filtration, an isoelectric point of about 7.6 using chromatofocusing, and an optimal pH range of about 3.8–4.5.

2. The sialidase of claim 1, wherein said sialidase is capable of hydrolyzing 4-methylumbelliferyl$\alpha$-ketoside of KDN, KDN$\alpha$2→3Gal$\beta$1→4GlcCer or KDN$\alpha$2→6N-acetylgalactosaminitol to yield KDN.

* * * * *